(12) United States Patent
Bates et al.

(10) Patent No.: US 6,361,499 B1
(45) Date of Patent: *Mar. 26, 2002

(54) MULTIPLE ANGLE NEEDLE GUIDE

(75) Inventors: John D. Bates, Kalona; David W. Best, Marion; Craig Cermak, Riverside; Brett Severence, Iowa City; David F. Schultz, Marion, all of IA (US)

(73) Assignee: CIVCO Medical Instruments Inc., Kalona, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/154,416

(22) Filed: Sep. 16, 1998

(51) Int. Cl.⁷ .................................................. A61B 8/14
(52) U.S. Cl. ....................................... 600/461; 600/464
(58) Field of Search .............................. 600/437, 459, 600/461, 464; 604/117, 116, 272; 128/759; 606/1, 108, 130

(56) References Cited

U.S. PATENT DOCUMENTS

| | | | | |
|---|---|---|---|---|
| 4,469,106 A | * | 9/1984 | Harui | 600/437 |
| 4,497,325 A | | 2/1985 | Wedel | |
| 4,898,178 A | | 2/1990 | Wedel | |
| 4,899,756 A | * | 2/1990 | Sonek | 600/461 |
| 5,052,396 A | * | 10/1991 | Wedel et al. | 600/461 |
| 5,076,279 A | * | 12/1991 | Arenson et al. | 600/461 |
| 5,196,019 A | * | 3/1993 | Davis et al. | 606/130 |
| 5,494,039 A | * | 2/1996 | Onik et al. | 600/461 |
| 5,623,931 A | | 4/1997 | Wung et al. | |
| 5,758,650 A | * | 6/1998 | Miller et al. | 600/461 |
| 5,941,889 A | * | 8/1999 | Cermak | 606/130 |

* cited by examiner

*Primary Examiner*—Marvin M. Lateef
*Assistant Examiner*—Ali M. Imam
(74) *Attorney, Agent, or Firm*—Merchant & Gould P.C.

(57) ABSTRACT

A needle guide for use in imaging analysis, such as ultrasound analysis, is provided having a mounting base secured to the imaging instrument. A needle guide is configured to be removably secured to the pivoting portion of the mounting base. The needle guide has a rotational needle retainer member that is configured to retain a needle by securing the needle within a slot on the needle guide.

21 Claims, 6 Drawing Sheets

FIG. 6A
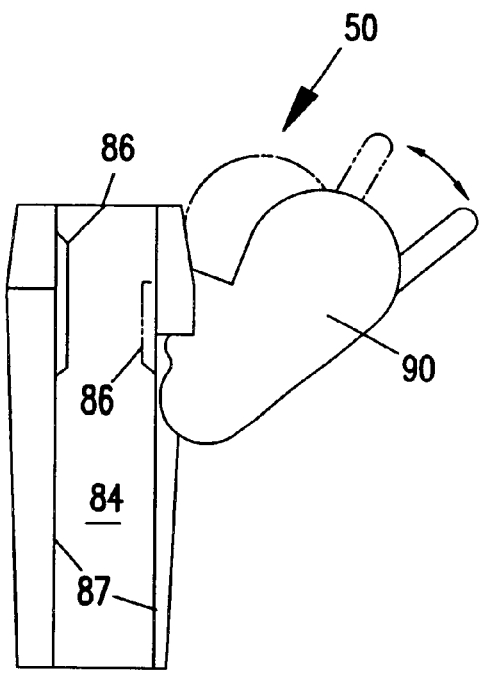
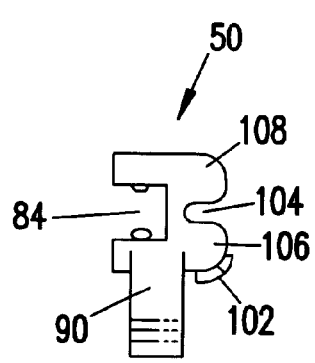
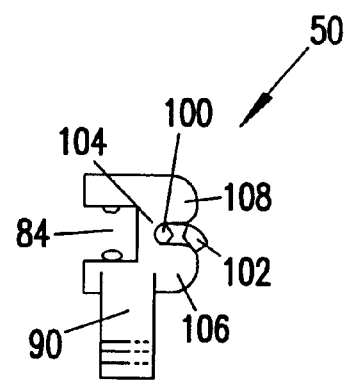
FIG. 6B    FIG. 6C

MULTIPLE ANGLE NEEDLE GUIDE

FIELD OF THE INVENTION

The present invention relates to a needle guide for a medical imaging instrument. More particularly, the invention is directed to a method and apparatus for a needle guide system for use in guiding needles into selected locations of a patient relative to a medical instrument imaging sensor. The needle guide method and apparatus provide improved attachment to the medical imaging sensor, improved access and removability of the needle, and improved insertion of a needle into the needle guide.

BACKGROUND

Imaging instruments, such as ultrasound probes, computed tomography scanners (CT Scanners), and magnetic resonance imagers (MRI) have revolutionized the manner in which many important medical procedures are performed. Each of these medical instruments utilizes non-invasive imaging techniques to explore and assess the condition of sub-dermal tissue. As a result of this non-invasive imaging ability, diagnostic and therapeutic protocol's have been developed that allow for the provision of many highly successful and safe procedures with a minimum of disturbance to patients.

Ultrasound, for example, has received widespread acceptance as a useful diagnostic tool. Ultrasound is particularly well suited for obstetrics, where real-time scanners create a continuous image of a moving fetus that can be displayed on a monitoring screen. The image is created by emission of very high frequency sound waves from a transducer placed in contact with the mother's skin. Repeated arrays of ultrasonic beams scan the fetus and are reflected back to the transducer, where the beams are received and the data transmitted to a processing device. The processing device can analyze the information and compose a picture for display on the monitoring screen. Relative measurements may be made, and the gestational age, size and growth of the fetus can be determined. In some circumstances, a needle is guided into the amniotic fluid in order to retrieve a fluid sample for analysis. These samples can be useful for diagnosing irregular conditions and to indicate that prenatal care is necessary for the fetus.

Ultrasound probes, and other imaging instruments, are also used for a variety of other purposes, such as identifying the existence, location, and size of tumors, as well as the existence of other medical conditions, including the atrophy or hypertrophy of bodily organs. While such imaging techniques are primarily performed on humans, similar techniques are often used by veterinarians to diagnose and treat a wide variety of animals, such as sheep, cows, horses, and pigs.

For many imaging applications, it is desirable that a needle, biopsy instrument, catheter, or other thin instrument be inserted into the body of a patient in order to remove a biopsy sample or to perform other medical procedures. It is normally desirable that the thin instrument or needle be guided to a specific position within the body of the patient. Various guide devices have been designed for assisting in guiding the instrument. Many of these guides are fixed-angle devices with limited functionality because they have limited control over needle placement compared to a needle guide that allows selection of multiple angles. In addition, many of these devices do not permit the placement of more than one needle into a patient at one time or they do not make such multiple placements easy.

Also, certain of these devices do not allow the needle to be easily inserted and removed from the needle guide, particularly while the needle is in the patient. One problem associated with the removal of needles from traditional needle guides is that the needle rotates or undergoes undesirable lateral movement during insertion and removal. Such lateral movement is characterized by movement of the needle parallel to the body surface (i.e., sideways) rather than into and out of the patient. This rotation and movement can be problematic because it alters the location of the needle and can create uncomfortable movement in the needle that is a distraction to patients. Even a small amount of movement is undesirable in many circumstances.

Another significant problem associated with some existing needle guides is that the guide mechanism is attached to the exterior of the imaging instrument by a bracket that wraps around the base of the sensor. These brackets can be quite expensive, adding hundreds of dollars to the cost of the needle guide. While such brackets securely hold the needle guide, they can create problems with maintaining the device in a sterile condition, and are often not well suited to be used with a sterile cover, such as a latex film, placed over the imaging instrument. Such covers are increasingly desirable in order to maintain the ultrasound sensor in a sterile environment. The covers reduce the likelihood of contamination between patients and reduce the cost of medical procedures by minimizing sterilization costs.

One challenge of working with latex and similar polymer based covers is that they have a high coefficient of friction and are subject to binding when in contact with moving pieces of an imaging sensor or needle guide. Such binding can lead to tears or punctures of the cover. For example, some prior art imaging sensors have removable pieces that are frictionally fit over a latex cover. Such designs are problematic because they can be difficult to fit and remove, as well as cause problems with binding and an ensuing risk of tearing. Consequently, a need exists for an improved needle guide system.

Such improved needle guide system should permit a needle to be directed into a patient and be removable from the patient without unnecessary lateral movement or rotation of the needle. The needle guide system should also reduce or eliminate the need for a bracket used to secure the needle guide to the imaging instrument.

SUMMARY OF THE INVENTION

The present invention is directed to a needle guide system for use in guiding a needle into a patient who is undergoing imaging analysis with an imaging instrument. This needle guide system includes a mounting base and a needle guide. In certain implementations, the mounting base is configured to pivot. The pivoting portion of the mounting base is configured to pivot along at least one axis, and the needle guide is removably secured to the pivoting portion of the mounting base. The needle guide has a rotatable needle retainer member configured to securely retain a needle in a slot, while still allowing removal from the guide with minimal rotation and movement.

Specific implementations of the needle guide system of the present invention are designed such that the system may be used with a protective cover placed over the mounting base, thereby enveloping the imaging instrument and the mounting base. The needle guide is configured to be removably secured to the mounting base over the protective cover, without the development of significant kinetic friction between the protective cover and the needle guide during mounting and removal of the needle guide. As such, the needle guide may be placed on the pivoting portion of the mounting base, and removed therefrom, with minimal mechanical stress to the protective cover, thereby preventing holes in the protective cover from developing and maintaining a sterile environment around the imaging instrument.

In other implementations, the needle guide system is designed such that the mounting base is placed over the protective cover. In such implementations, the protective cover is positioned between the mounting base and the imaging instrument. The mounting base is placed on the imaging instrument with minimal stress to the protective cover, which also avoids consequent holes generated from this stress.

In addition, in specific implementations of the present invention, the needle guide system further includes a movable locking member having an unlocked configuration in which the locking member does not apply pressure to the mounting base, while also having a locked configuration in which the locking member does apply pressure to the mounting base. The locking member is alternated between a locked and unlocked configuration during removal without applying significant kinetic friction to the protective cover.

In certain implementations, the pivoting portion of the mounting base pivots around an axis occupied by a pin. In other implementations, the pivoting portion is integrally connected to a non-pivoting portion of the base by a flexible connecting portion, and the pivoting portion pivots around an axis formed by flexing of the connecting portion. In this implementation, the pivoting portion does not pivot around a pin.

In certain embodiments of the present invention, the pivoting portion of the mounting base is configured to be locked in one of a plurality of preset positions. The needle retainer member pivots along an axis parallel to the length of the needle, permitting needles of multiple sizes to be held between the needle retainer member and a first surface of the needle guide. The needle is removed from the needle guide by opening the rotational gate member holding the needle in place. A plurality of interchangeable needle retainer members are used to permit needles of various sizes to be used.

The above summary of the present invention is not intended to describe each discussed embodiment of the present invention. This is the purpose of the figures and the detailed description which follow.

BRIEF DESCRIPTION OF THE DRAWINGS

Other aspects and advantages of the invention will become apparent upon reading the following detailed description and references to the drawings, in which:

FIG. 6A is a back elevational view of a removable needle guide constructed in accordance with the present invention.

FIGS. 6B and 6C are top elevational views of a removable needle guide constructed in accordance with the present invention.

While the invention is susceptible to various modifications and alternative forms, specifics thereof have been shown by way of example and drawings, and will be described in detail. It should be understood, however, that the intention is not to limit the invention to particular embodiments described. On the contrary, the intention is to cover modifications, equivalents, and alternatives falling within the spirit and scope of the invention as defined by the appended claims.

DETAILED DESCRIPTION

Figure 1:
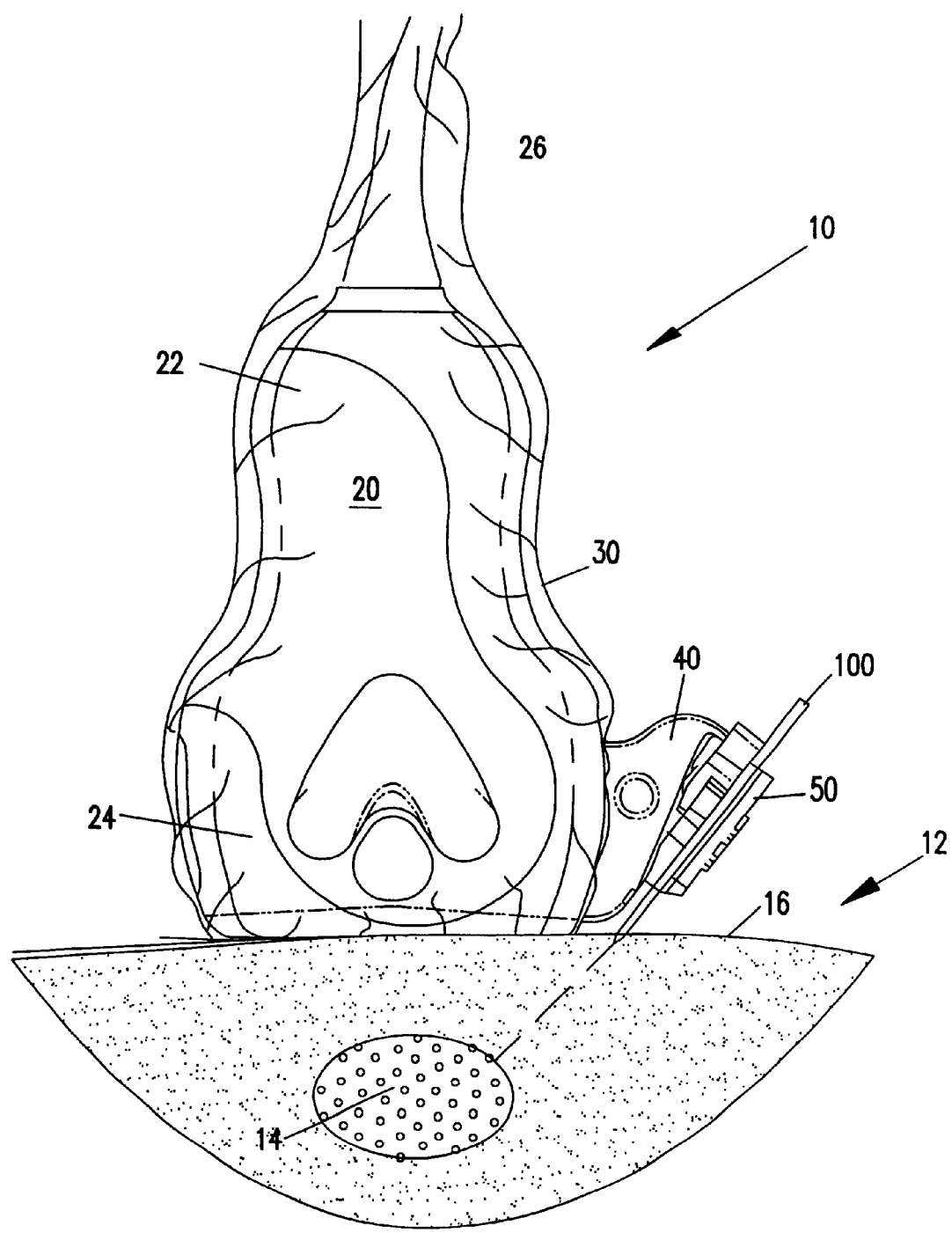
FIG. 1 is a side elevational view of a needle guide system constructed in accordance with the present invention, showing the needle guide system installed on an ultrasonic probe having a protective cover.

Referring now to the figures wherein like numerals identify like elements throughout the drawings, FIG. 1 shows a side elevational view of a needle guide system constructed in accordance with the present invention. Needle guide system 10 includes an ultrasound probe 20. A protective cover 30 encases the ultrasound probe 20. A mounting base 40 is positioned outside of the protective cover 30 in the depicted implementation. A needle guide 50 is fitted onto the mounting base 40. A needle 100 is shown retained in the needle guide 50.

Protective cover 30 provides a sterile seal over the ultrasound probe 20 such that it remains free of contamination during most medical procedures. As such, the enclosed elements of the needle guide system 10 do not come in contact with bodily fluids and reduce the risk of transfer of disease-causing vectors between the needle guide system and the patient.

The protective cover 30, which is normally disposable, prevents contamination between patients as well as provides a low-cost method of reducing sterilization requirements of the ultrasound probe and needle guide system. The needle guide 50 is outside of the protective cover, and therefore is normally disposed of after the medical procedure or is sterilized using conventional methods between procedures.

Ultrasound probe 20 includes a handle 22 connected to a sensor 24. Handle 22 is typically configured to be grasped by the hand of a medical practitioner who is conducting an imaging analysis with the ultrasound probe 20. However, the handle 22 may alternatively be held, or additionally be held, by a mechanical brace or adjusting device for holding the ultrasound probe in a specific adjustable position. The sensor 24 includes an ultrasound transducer and receiver in specific implementations of the present invention, and sends out and receives sound waves that are transmitted to diagnostic and display equipment (not shown). As stated earlier, ultrasound probe 20 is substituted for other medical imaging probes in alternative implementations of the invention.

Protective cover 30 is normally constructed of a thin polymer film, most often of natural or synthetic latex. While protective cover 30 will encompass the entire ultrasound probe and needle guide mounting base 40 in certain implementations, it is preferred that the protective cover 30 include an opening at a cable terminus 26. Cable terminus 26 leads to the diagnostic and display equipment (not shown). Alternatively, in some implementations, the needle guide system 10 is designed such that the mounting base 40 is placed over the protective cover 30 (as shown in FIG. 1). In such implementations, the protective cover is positioned between the mounting base 40 and the ultrasound probe 20. The mounting base 40 is placed on the ultrasound probe 20 with minimal stress to the protective cover 30, which also avoids consequent holes in the protective cover generated from this stress.

As is indicated in FIG. 1, the ultrasound probe 20 may be placed in a position proximate a patient 12. In FIG. 1, patient 12 is depicted in fractional view showing a target zone 14 and an outer surface or skin 16. Target zone 14 may be any of a number of locations within the body of a human or animal which is desirably accessed by a needle or other thin medical instrument, such as a catheter or biopsy probe. Target zone 14 may be, for example, a tumor of which a biopsy sample is desired, or a volume of amniotic fluid from which a sample is desired.

Figure 2A:
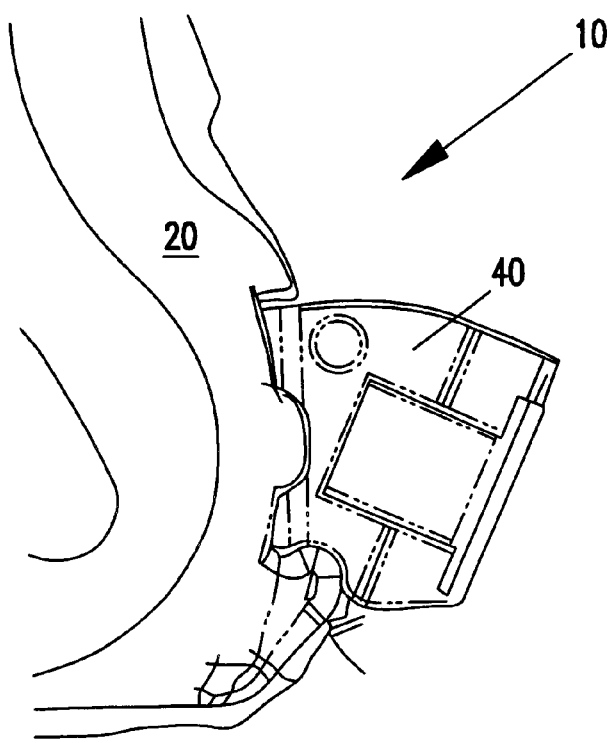
FIG. 2A is a fragmentary side elevational view of a needle guide system constructed in accordance with the present invention, the system having an integrated needle guide and mounting base.
Figure 2B:
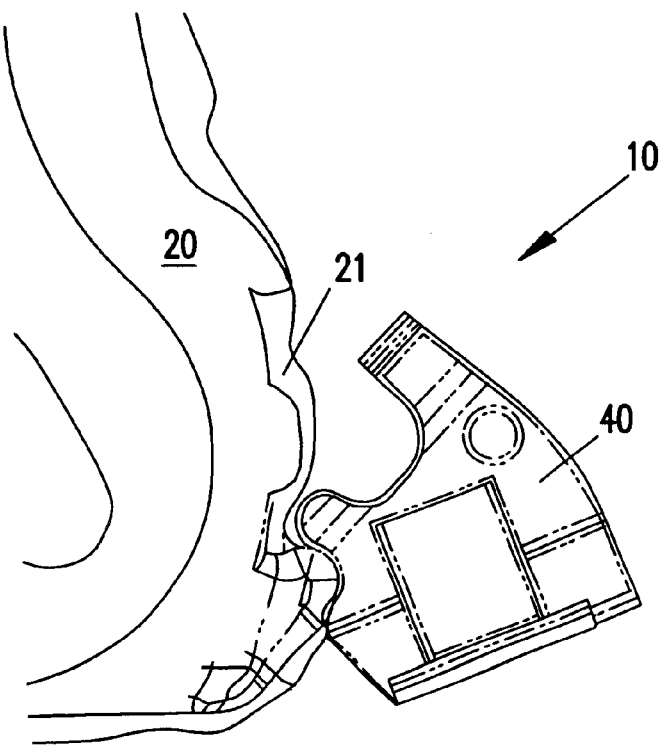
FIG. 2B is a fragmentary side elevational view of a needle guide system constructed in accordance with the present invention, the system having an integrated needle guide and mounting base.

Referring now to FIG. 2A and FIG. 2B, mounting base 40 is shown with an integrated needle guide such that it is directly connected to the ultrasound probe, without the use of a bracket. The mounting base 40 is shown mounted to the ultrasound probe 20 in FIG. 2A, and is shown in the process of being attached or removed in FIG. 2B by pivoting the top portion of the mounting base 40 outward. It will be observed that mounting base 40 is secured in a depression 21 in the ultrasound probe 20. When the mounting base is not secured to the probe 20, a cover (not shown) is optionally placed over the depression 21 to prevent contamination of the depression as well as to provide a comfortable grip for applications that do not require a needle guide. The mounting base 40 shown in FIGS. 2A and 2B shows the needle guide integrally formed with and mounted to the mounting base 40.

Additional means of attaching the mounting base 40 to the ultrasound probe 20 are also contemplated by the invention. In specific implementations, the mounting base 40 is constructed to slide into the body of the ultrasound probe. In other implementations, the mounting base rotates into the body of the ultrasound probe. As described above, in yet other implementations, the mounting base is removably secured to the outside of the ultrasound probe without the use of a bracket. In these implementations, the needle guide is secured with a removable mounting base that is secured either on top of the protective cover, or directly to the ultrasound probe and then the protective cover is added over both the probe and the mounting base.

Figure 3A:
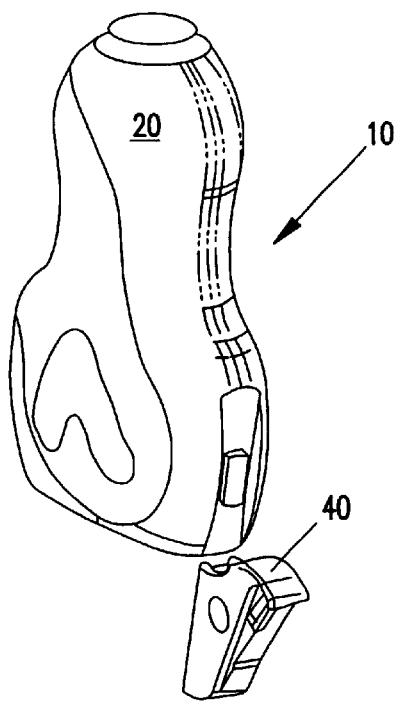
FIG. 3A is a first perspective view of an ultrasound probe and mounting base constructed in accordance with the present invention.
Figure 3B:
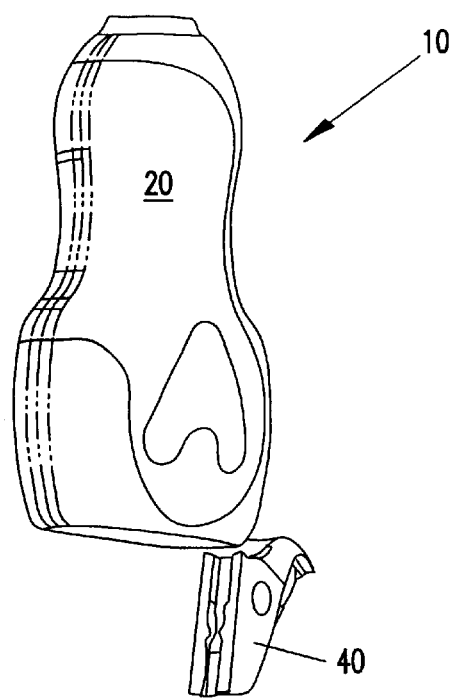
FIG. 3B is a second perspective view of an ultrasound probe and mounting base constructed in a accordance with the present invention.

Referring now to FIGS. 3A and 3B, an additional implementation of the removable mounting base 40 is depicted such that the mounting base 40 is slidably attached and locked to the ultrasound probe 20. It will be noted that a single ultrasound probe can be configured to receive a friction-fit mounting base on one end (shown in FIG. 2A and 2B); and a slidably secured mounting base on the other end (shown in FIG. 3A and 3B) so that greater flexibility is allowed in selecting a manner of securing the mounting base to the probe 20.

Figure 4A:
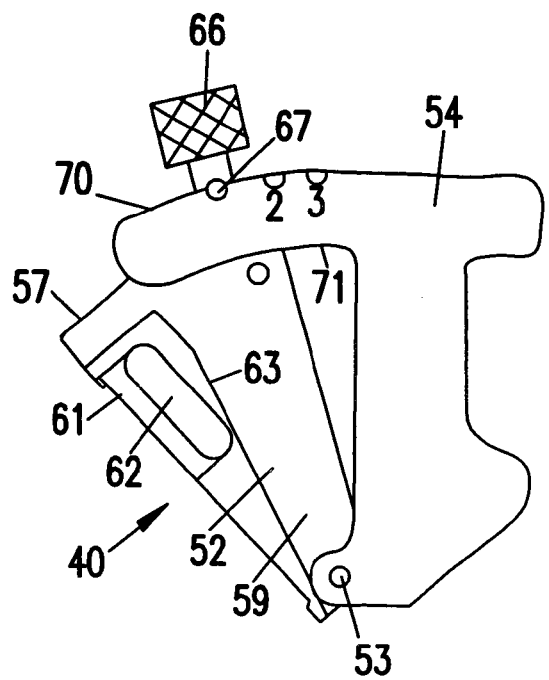
FIG. 4A is a fragmentary elevational view of a portion of a needle guide mounting base, constructed in accordance with the present invention, showing a first side of the mounting base.
Figure 4B:
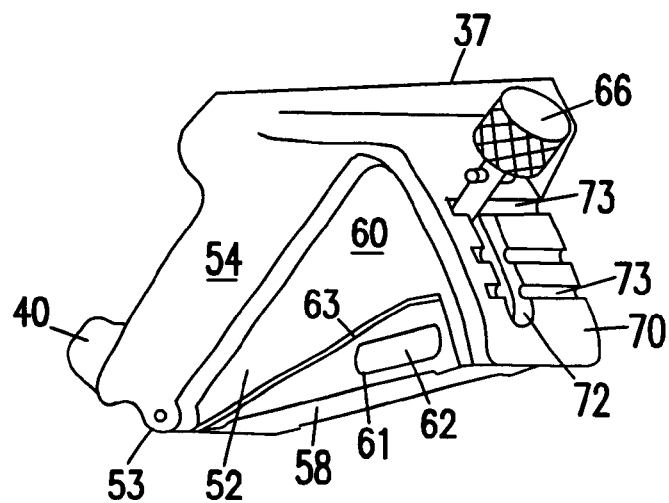
FIG. 4B is a fragmentary perspective view of a needle guide mounting base constructed in accordance with the present invention, showing a second side of the mounting base.

In certain implementations, the needle guide mounting base 40, mentioned above, adjusts in angle in order to direct needles (or other medical instruments) at various orientations into the body of a patient. Referring now to FIG. 4A and FIG. 4B, a fragmentary elevational view and a fragmentary perspective view of a portion of an adjustable-angle needle guide mounting base 40 are shown. In both figures, the mounting base 40 is depicted without the needle guide 50 so as to show the elements of the mounting base 40 that are configured to retain the needle guide 50. It should also be appreciated that FIG. 4A and FIG. 4B show opposing sides of the mounting base. FIG. 4A shows a first side 59 of the mounting base 40, and FIG. 4B shows a second side 60, of the mounting base 40.

As is evident from FIG. 4A and FIG. 4B, the mounting base has a pivoting portion 52 and a non-pivoting portion 54. Pivoting portion 52 is mounted generally within non-pivoting portion 54. Pivoting portion 52 is configured to pivot around an axis 53. Thus, pivoting portion 52 and non-pivoting portion 54 are secured to one another proximate axis 53.

The orientation shown in FIG. 4A permits the needle to enter tissue at a more acute angle with respect to the surface 16 of the patient 12 than the angle in FIG. 4B. It will also be appreciated that multiple angles may be chosen, and that the angles shown in the figures are demonstrative of such angles, but not exclusive. Other angles, both more acute and more oblique, are envisioned by the inventor as manners of practicing the present invention.

The manner in which the pivoting portion 52 pivots within the non-pivoting portion 54 is evident. While pivoting portion 52 pivots with respect to non-pivoting portion 54, in certain implementations of the present invention a top surface 57 of the non-pivoting portion 52 comes in contact with the inner surface 71 of the non-pivoting portion 54 (See FIG. 4A). The top surface 57 and inner surface 71 of the pivoting and non-pivoting portions 52, 54 frictionally engage one another in certain implementations of the present invention. The frictional engagement may be very minor, so as to simply provide a slight resistance during adjustment of the angle, or may be of a greater magnitude so as to hold the pivoting portion 52 in place during performance of the imaging analysis. It should also be appreciated that in certain implementations the top surface 54 of the pivoting portion 52 and the inner surface 71 of the non-pivoting portion 54 do not make contact with one another, and thus there is no friction between the two portions. A channel may be positioned within the inner surface 71 of the non-pivoting portion 54 to facilitate the alignment and stability of the non-pivoting portion 52 with respect to the pivoting portion 54. As such, the inner surface 71, in specific implementations, extends over the top surface 57 along the sides 59, 60 of the pivoting portion 52.

A locking pin 66 is shown as a mechanism for retaining the pivoting portion 52 in a selected position. Locking pin 66 extends through the outer surface 70 of the non-pivoting portion 54 and into the pivoting portion 52. Pin 66 is configured to travel along a channel 72 in the non-pivoting portion 54 of the mounting base 40. In certain embodiments, the pin 66 includes one or two side tabs 67, shown in FIG. 4A and FIG. 4B. The side tabs 67 are configured to engage transverse slots 73 positioned in the outer surface 70 of the non-pivoting portion 54. The slots 73 are, in some embodiments, shallow depressions into which the tabs 67 may be placed in order to "lock" the pivoting portion 52 in place. While the embodiment depicted shows three different slots 73, more or less slots may be included in various embodiments of the present invention. Also, it will be appreciated that numbers, or other designations, may be made in the side of the mounting base 40 (as shown in FIG. 4A) to designate the position of the pivoting portion 52. Such numbers or designations may be sequential integers, as shown, to depict a numerical slot position; or alternatively, the numbers may be an actual degree measurement indicating the incident angle of the needle or medical instrument as it enters the skin 16 of a patient 12 (not shown).

In operation, the embodiment depicted in FIG. 4A and FIG. 4B has the angle between the pivoting and non-pivoting portions 52, 54 adjusted by applying an upward force on the pin 66 (shown in FIG. 4A), such that the side tabs 67 are lifted out of the transverse slots 73 (shown in FIG. 4B), so that the pivoting portion may be moved (FIG. 4B) to a new position, and the pin 67 pressed back into place to lock the pivoting portion 52 into a new position.

Continuing to refer to FIG. 4A and FIG. 4B, the portion of the mounting base 40 that is configured to receive the needle guide 50 will be described. The mounting base 40 is configured such that a needle guide 50 may be secured to the base 40. In certain implementations of the present invention, the base 40 permits the mounting of the needle guide 50 with minimal kinetic friction, and uses a compressive force to retain the needle guide 50. Kinetic friction refers here to the friction generated when two surfaces move with respect to one another while in contact.

As noted above, the embodiments shown in FIG. 4A and FIG. 4B example implementations of how the mounting base and ultrasound probe are secured to one another. The mounting base 40 is secured to the ultrasound probe 20 in other manners in alternative embodiments. In specific implementations, the mounting base is constructed to slide into the body of the ultrasound probe. In other implementations, the mounting base rotates into the body of the ultrasound probe. In yet other implementations, the mounting base is removably secured to the outside of the ultrasound probe without the use of a bracket. In these implementations, the ultrasound probe is secured by way of a removable mounting base that is secured either on top of the protective cover, or directly to the ultrasound probe and then the protective cover is added over both the probe and the mounting base.

The base 40 is specifically configured to retain the needle guide 50. On each of the two sides 59, 60 is a receiver recess 61. In specific implementations, receiver recess 61 is a shallow depression, generally uniform in depth, along a portion of the first and second sides 59, 60. In addition, in the embodiment depicted, a locking recess 62 is shown in each of the receiver recesses 61. Locking recess 62 is a depression in the first and second sides 59, 60, even deeper than the receiver recesses 61. In specific implementations, the locking recesses 62 are generally concave depressions without abrupt transitions between the locking recesses 62 and the receiver recesses 61. In addition, it will be noted in FIG. 4A and FIG. 4B that the receiver recesses 61 have a transition ridge 63 along the periphery, at the junction of the receiver recess 61 and the surrounding first and second sides 59, 60 of the pivoting portion 52.

Figure 5A:
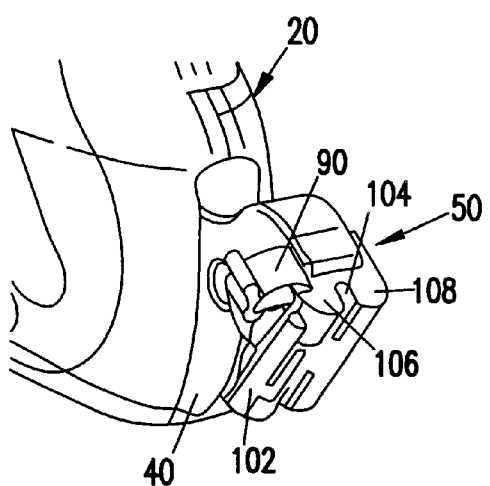
FIGS. 5A, 5B and 5C are perspective views of a needle guide and mounting base constructed in accordance with the present invention.
Figure 5B:
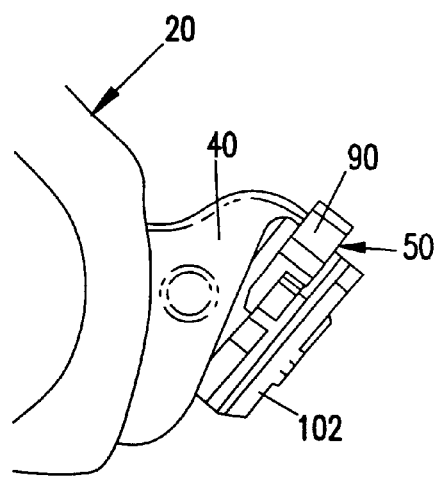
Figure 5C:
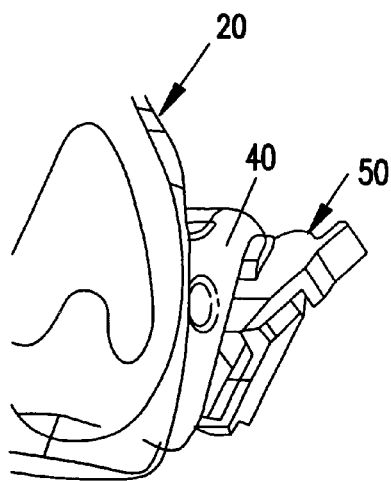

In FIG. 5A, 5B, and 5C, the needle guide 50 is shown from various perspectives fitted over the mounting base 40. Needle guide 50 includes a swivel 90 that locks the needle guide 50 to the mounting base 40. In addition, needle guide 50 includes a slot 104 configured to receive a needle. The needle is held within slot 10 by a rotational gate member 102 that pivots to lock the needle within the slot without rotation of the needle itself. Thus, in operation, the needle is placed within slot 104 and then the rotational gate member is rotated around to retain the needle in place. In the embodiment shown, the slot 104 is formed between two ridges 106, 108. The rotational gate member 102 pivots around the first ridge 104 when being closed, and comes to rest partially between ridges 106 and 108 when fully closed and locked.

The interior or back of the needle guide 50 is shown depicted in FIG. 6A, and the top of the needle guide 50 is shown depicted in FIG. 6B, and 6C. In FIG. 6A, the locking protrusions 86 are shown. These locking protrusions are configured to engage the locking recesses 62 of the pivoting portion 52. Likewise, the inner side walls 87 of the needle guide fit into the receiver recesses 61 of the pivoting portion 52, to give the configuration shown generally in FIG. 1. The inner back wall 88 of the needle guide 50 fits around the outer edge of the pivoting portion 52, such that the volume 84 defined by the inner side walls 87 and inner back wall 88 is occupied by part of the pivoting portion 52.

In the embodiment shown, the needle guide 50 is locked to the pivoting portion 52 of the mounting base 40 by moving the locking swivel 90 between a locked and an unlocked position (see FIG. 6A). In the locked position (shown in phantom lines in FIG. 6A), the locking protrusion 86 integrally formed with the locking swivel 90 may enter and engage one of the locking recesses 62 of the pivoting portion 52.

It will also be appreciated that in the present invention the retractable characteristic of the locking protrusion 86 of the locking swivel 90 allows for placement of a tight-fitting needle guide 50 over a protective cover 30 and mounting base 40 with low kinetic friction. Once in place over the mounting base, the locking swivel 90 is "locked" so as to press the two locking protrusions 86 into corresponding locking recesses 62, thereby securely retaining the needle guide 50 to the base 40. The friction between the pieces is reduced because the locking recess 86 on the locking swivel 90 is retracted during the attachment and removal process, thereby expanding the width of mounting socket 84 until the swivel 90 is locked in place. This design reduces the amount of "dragging" between the needle guide 50 and the cover 30 and mounting base 40, thereby preventing binding and potential puncture or damage to the cover 30.

In reference to FIGS. 6B and 6C, a top view of the needle guide 50 is shown with rotational gate member 102 in both an open (FIG. 6B) and a closed (FIG. 6C) configuration. In FIG. 6C, the needle 100 is held in slot 104 by the rotational gate member 102. The slot 104 is formed between ridges 106 and 108 While the embodiments described above secure the needle guide 50 to a mounting base 40, it will also be appreciated that the needle guide 50 may be secured to a mounting base 40 that does not pivot, but rather has one secured position. While such embodiments may not include an adjustable angle, they still benefit from the attachment of a needle guide over a protective cover with reduced kinetic friction. The protective cover is optionally placed over the mounting base with the needle guide subsequently attaching over the cover and the base.

In certain implementations of the invention, the needle guide is integrally formed with the mounting base, and is thus a single piece. In such implementation, the combined needle guide and mounting base are either both disposable or both reusable.

It will also be appreciated that the present invention benefits from the fact that the needle 100 may be removed from slot 104 of the needle guide 50 without removal of the needle from the patient by pivoting the rotational gate member 102 backwards (as shown in FIG. 6B). Note that the needle is released without rotation or movement of the needle during opening of the gate member 102. Likewise, the needle 100 may be reinserted into the needle guide 50 without significant disruption or agitation of the needle. This allows a second, third, or more needles (or other instruments) to be inserted into a patient with one needle guide. Notably, the present invention allows removal of the needle 100 from the needle guide 50 without rotation or other significant agitation or movement of the needle 100. The needles can even be installed at variable angles by adjusting the angle between the pivoting and non-pivoting portions 52, 54 between placements of needles. It will also be noted that in the embodiments described, the protective cover is not impacted by the insertion or removal of the needles, thereby preserving the sterile conditions mentioned above.

It will be appreciated that, although the implementation of the invention described above is directed to an ultrasound probe, the present device may be used with other types of medical imaging systems, and is not limited to ultrasound probes. In addition, while the present invention has been described with reference to several particular implementations, those skilled in the art will recognize that many changes may be made hereto without departing from the spirit and scope of the present invention.

We claim:

1. A needle guide system for guiding a needle into a patient undergoing imaging analysis, the needle guide system comprising:
   a mounting base integrally formed with the imaging instrument; and
   a needle guide configured to be removably secured to the mounting base, the needle guide having a rotatable needle retainer member configured to releasably retain a needle between the needle retainer member and a first surface of the needle guide, such that the needle may be released from the needle guide without substantial movement of the needle.

2. The needle guide system according to claim 1, wherein the mounting base integrally formed with the imaging instrument includes a retaining surface configured to receive the needle guide.

3. The needle guide system according to claim 2, further comprising:
   a removable cover configured to secure to the retaining surface of the mounting base, the removable cover optionally protecting and concealing the retaining surface when the needle guide is not secured to the mounting base.

4. The needle guide system according to claim 2, wherein the mounting base is rotationally secured and formed to the imaging instrument such that the mounting base may be rotated or slid to conceal the retaining surface.

5. The needle guide system of claim 1, wherein a protective cover may be placed over the mounting base, and the needle guide is configured to be removably secured to the mounting base over the protective cover without the development of significant kinetic friction between the protective cover and the needle guide.

6. The needle guide system of claim 1, further comprising:
   a pivoting portion of the mounting base configured to pivot along at least one axis, the pivoting portion providing a plurality of angles at which the needle guide may be arranged relative to the body surface of a patient.

7. The needle guide system of claim 6, wherein the pivoting portion of the mounting base pivots around an axis occupied by a pin.

8. The needle guide system of claim 6, wherein the pivoting portion is integrally connected to a non-pivoting portion of the mounting base by a flexible connecting portion, and the pivoting portion pivots around an axis formed by flexing of the connecting portion.

9. The needle guide system of claim 6, wherein the pivoting portion of the mounting base is configured to be locked in one of a plurality of pre-set positions.

10. The needle guide system of claim 6, wherein the needle retainer member is slidably secured to the needle guide and is interchangeable with a second needle retainer member.

11. The needle guide system of claim 6, wherein the needle retainer member includes a slot configured to receive a needle, and a rotatable gate member for locking the needle within the slot of the needle retainer member.

12. The needle guide system of claim 11, wherein the rotatable gate member for locking the needle is configured to close without substantially rotating the needle.

13. The needle guide system of claim 1, wherein the imaging instrument is an ultrasound probe.

14. A needle guide for guiding a needle into a patient undergoing imaging analysis, the needle guide comprising:
   a base portion configured to be removably secured to a mounting base;
   a needle-receiving slot, the slot configured to receive a needle by lateral insertion of a needle.
   a rotatable needle retainer member configured to releasably retain a needle within the needle receiving slot, wherein the rotatable needle retainer member is configured to release a needle without rotating the needle during release.

15. The needle guide according to claim 14, wherein the needle-receiving slot is generally concave in cross section.

16. The needle guide according to claim 14, wherein the needle-receiving slot includes a plurality of ribs that lock the needle retainer member closed.

17. A needle guide system for guiding a needle into a patient undergoing imaging analysis, the needle guide system comprising:
   a mounting base integrally formed with the imaging instrument; and
   a needle guide configured to be removably secured to the mounting base, the needle guide comprising:
      a needle-receiving slot, the slot configured to receive a needle by lateral insertion of a needle, and
      a rotatable needle retainer member configured to releasably retain a needle between within the needle receiving slot.

18. The needle guide system according to claim 17, wherein a protective cover may be placed over the mounting base, and the needle guide is configured to be removably secured to the mounting base over the protective cover without the development of significant kinetic friction between the protective cover and the needle guide.

19. The needle guide system according to claim 17, wherein the mounting base is rotationally secured and formed to the imaging instrument such that the mounting base may be rotated to conceal the retaining surface.

20. The needle guide system according to claim 17, wherein the mounting base is secured to the imaging instrument such that the mounting base may be slid into and out of the imaging instrument.

21. The needle guide system according to claim 17, wherein the rotatable needle retainer member is configured to release a needle without rotating the needle during release.

* * * * *